(12) United States Patent
Viswanathan

(10) Patent No.: US 7,983,733 B2
(45) Date of Patent: Jul. 19, 2011

(54) SURGICAL NAVIGATION USING A THREE-DIMENSIONAL USER INTERFACE

(75) Inventor: Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1553 days.

(21) Appl. No.: 10/975,029

(22) Filed: Oct. 26, 2004

(65) Prior Publication Data

US 2006/0100505 A1  May 11, 2006

(51) Int. Cl.
*A61B 5/05* (2006.01)
(52) U.S. Cl. ........ 600/417; 600/411; 600/410; 600/415; 600/423; 600/429
(58) Field of Classification Search .............. 600/411, 600/423, 424, 427, 429, 410, 415, 417; 604/164.01, 604/96.01, 20, 151–155, 164, 96
See application file for complete search history.

(56) References Cited

U.S. PATENT DOCUMENTS

| | | | | |
|---|---|---|---|---|
| 6,057,828 | A | 5/2000 | Rosenberg et al. | 345/156 |
| 7,048,716 | B1 * | 5/2006 | Kucharczyk et al. | 604/164.01 |
| 2003/0125752 | A1 * | 7/2003 | Werp et al. | 606/108 |
| 2005/0148848 | A1 * | 7/2005 | Guang et al. | 600/407 |

OTHER PUBLICATIONS

Enst et al. Initial Experience With Remote Catheter Ablation Using a Novel Magnetic Navigation System: Magnetic Remote Catheter Ablation. Circulation 2004;109;1472-1475; originally published online Mar. 15, 2004.*
Dario et al. Smart Surgical Tools and Augmenting Devices. IEEE Transactions on Robotics and Automation, vol. 19, No. 5, Oct. 2003.*
Ernst et al. Initial Experience With Remote Catheter Ablation Using a Novel Magnetic Navigation System: Magnetic Remote Catheter Ablation. Circulation 2004;109;1472-1475; originally published online Mar. 15, 2004.*
SensAble Technologies @ http://sensable.com.
Polhemus, three-dimensional scanning, position/orientation tracking system, eye tracking and head tracking systems @ http//www.polhemus.com.
Perspecta Spatial 3D http://www.actuality-systems.com.

* cited by examiner

*Primary Examiner* — Brian Casler
*Assistant Examiner* — Joel M Lamprecht
(74) *Attorney, Agent, or Firm* — Harness, Dickey & Pierce, P.L.C.

(57) ABSTRACT

A system for controlling a medical device in a patient. A display system displays an image of a volume of the patient in a virtual three-dimensional space. A stylus is controllable to actuate a virtual element in the virtual space. A navigation system controls the medical device in the patient volume based on a position of the actuated virtual element. This inherently three-dimensional interface allows a physician to actuate the medical device more intuitively than possible using a two-dimensional interface.

30 Claims, 2 Drawing Sheets

SURGICAL NAVIGATION USING A THREE-DIMENSIONAL USER INTERFACE

FIELD OF THE INVENTION

The present invention relates to systems for navigating a medical device within a patient and more particularly to navigation of a medical device using a three-dimensional user interface.

BACKGROUND OF THE INVENTION

During interventional surgery, devices such as catheters and guide wires are often navigated through the body to deliver therapy to anatomical sites deep within a patient's body, often following quite complex three-dimensional paths. For guidance, a physician may use fluoroscopy, magnetic resonance imaging (MRI), a localization system and/or other means of locating a medical device within the patient.

While the physician commonly uses his or her manipulative skills at the proximal end of the device in order to navigate the distal end of the device through the body, recent technological advances have made it possible to automate or semi-automate and thereby assist the process of navigation. For example, in one known magnetic navigation system, a device having a magnetic tip is steered by means of a magnetic field generated in the vicinity of the patient and directed by the operating physician. The physician may navigate the device from within, or remotely outside, the operating room.

Such remote actuation methods can greatly benefit from the use of a well-designed user interface. User interfaces are commonly provided in the form of a graphical user interface (GUI) and one or more associated input devices, for example, a two-dimensional display screen and a mouse or joystick. Manipulating the mouse or joystick with reference to a two-dimensional display, however, is intuitively and physically different from manually navigating a medical device along a three-dimensional and possibly constricted path in the subject.

SUMMARY OF THE INVENTION

The preferred embodiment of the present invention is directed to a system for controlling a medical device in a subject. A display system displays an image of at least part of an operating volume in the subject in a virtual three-dimensional space. A stylus is controllable to actuate a virtual element in the virtual space. A navigation system controls the medical device in the operating volume based on a position/orientation of the actuated virtual element.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF EMBODIMENTS

The following description of various embodiments of the invention is merely exemplary in nature and is in no way intended to limit the invention, its application, or uses.

Figure 1:
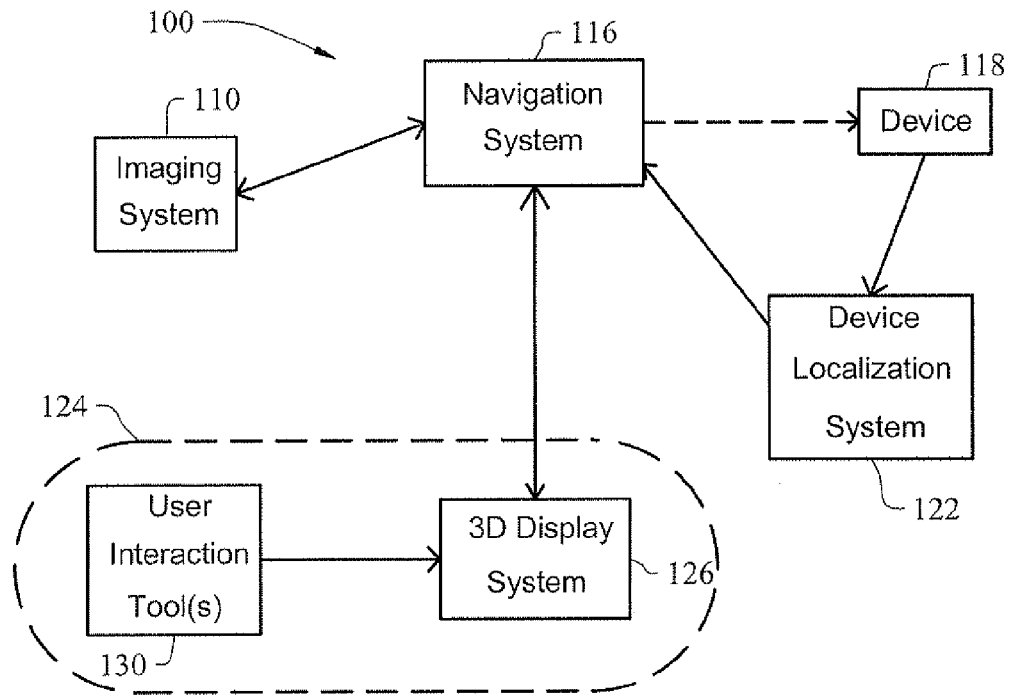
FIG. 1 is a block diagram of a system for controlling a medical device in the body of a patient in accordance with one configuration of the present invention.

A system for controlling a medical device in the body of a subject is indicated generally in FIG. 1 by reference number 100. The control system 100 includes a navigation system 116 that directly controls a medical device 118 by suitably actuating it. The medical device 118 may include, for example, a guide wire, a catheter, or a catheter over a guide wire. The invention may be practiced, however, in connection with any type of medical device that may be controllable within a patient using a navigation system. The navigation system 116 may control the device 118 by magnetic, electrostrictive, piezoelectric, thermal, mechanical, hydraulic or other means familiar to those skilled in the art.

The medical device 118 can be tracked and/or localized in space by a device localization system 122 using optical, electromagnetic, ultrasound, electrostatic or other means known to those skilled in the art. The localization system 122 communicates position data relative to the device 118 to the navigation system 116. The navigation system 116 interfaces with an imaging system 110 in which x-ray, magnetic resonance and/or other imaging means are used to provide an image of the device 118 within the patient.

A user interface 124 includes a three-dimensional (3D) display system 126 and a stylus 130 and/or other device operable by a user to interact with and communicate with the display system 126. The display system 126 is referred to herein as "3D" because it can display an image in such a way that a user of the system 126, for example, an operating physician, can perceive the displayed image as existing in three-dimensional space. The display system 126 communicates with the navigation system 116 as further described below.

The 3D display interface 124 can be based, for example, on stereoscopic image projection, stereoscopic image reflection, projection on rapidly rotating transparent or semi-transparent screens, or any other means familiar to persons skilled in the technology. The interface 124 could include, e.g., a stereoscopic computer screen display, head-mounted stereoscopic goggles, and/or and immersive three dimensional stereoscopic display employing mirrors. The display interface 124 can also include haptic feedback, as further described below.

Figure 2:
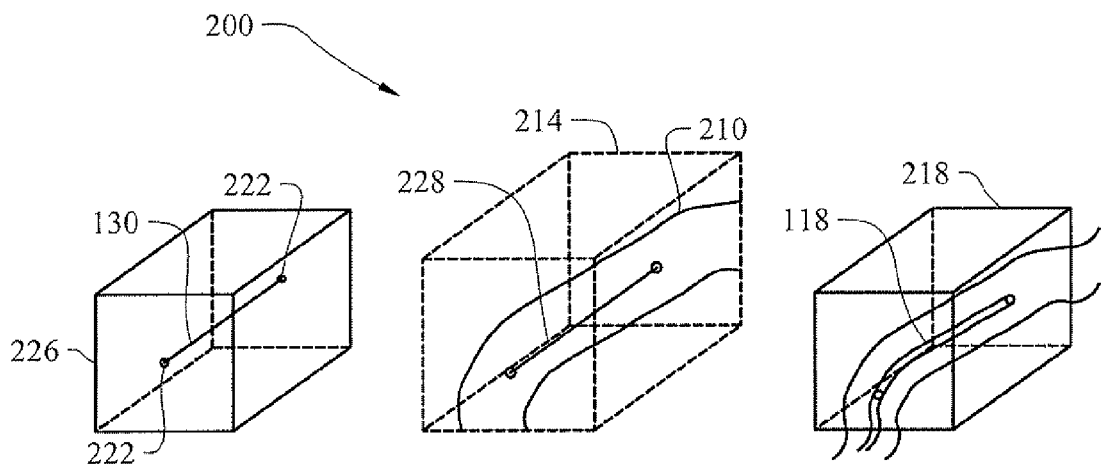
FIG. 2 is a perspective view of virtual and real spaces in accordance with one implementation of the present invention.

Virtual and real spaces in accordance with one implementation of the present invention are indicated generally in FIG. 2 by reference number 200. Referring to FIGS. 1 and 2, the display system 126 displays an image 210 in a three-dimensional virtual space 214. It should be understood that the virtual space 214 may be configured in various ways, dependent, for example, on the method used by the display system 126 for providing a three-dimensional display. In the Figures, the space 214 is represented as it might appear to a user of the system 100.

The image 210 is derived from a dataset that may have been previously acquired (e.g. pre-operatively or intra-operatively) by the imaging system 110 (or other imaging system) from a scan of the patient's anatomy, for example, from a computed tomography (CT) or magnetic resonance (MR) scan. The scan data set may describe a selected operating volume 218 within the subject's body (e.g., a site in which the device 118 is located) and can be displayed as one or more images by the display system 126. The data set may be acquired in some cases at the start of a medical procedure and/or just before the procedure starts, and in some cases may be pre-processed to extract desired anatomical regions, surfaces and the like.

The position and orientation of the stylus 130 can be tracked in space by means of mechanical, optical, electromagnetic, ultrasound or other methods. For example, the stylus 130 may include transmitters 222 that issue signals to receivers at known locations whereby position, orientation and/or movement of the stylus 130 in a real three-dimensional space 226 can be determined and tracked essentially in real time. Alternatively the stylus may include sensors 222 that receive signals from transmitters at known locations, whereby position, orientation and/or movement of the stylus in a real three-dimensional space 226b can be determined and tracked essentially in real time. Data describing the positioning and orientation of the stylus 130 can be registered, e.g., to "locations" or virtual coordinates, within the virtual three-dimensional display space 214 described by the display system 126. Thus the real stylus 130 can be registered and displayed as a "virtual stylus" 228 in the display space 214 and can be used for manipulating an image or object in three dimensions in the display space 214. Accordingly, the real stylus 130 could be used for manipulating the virtual stylus 228 and/or for editing the 3D image 210 in the display space 214.

Figure 3:
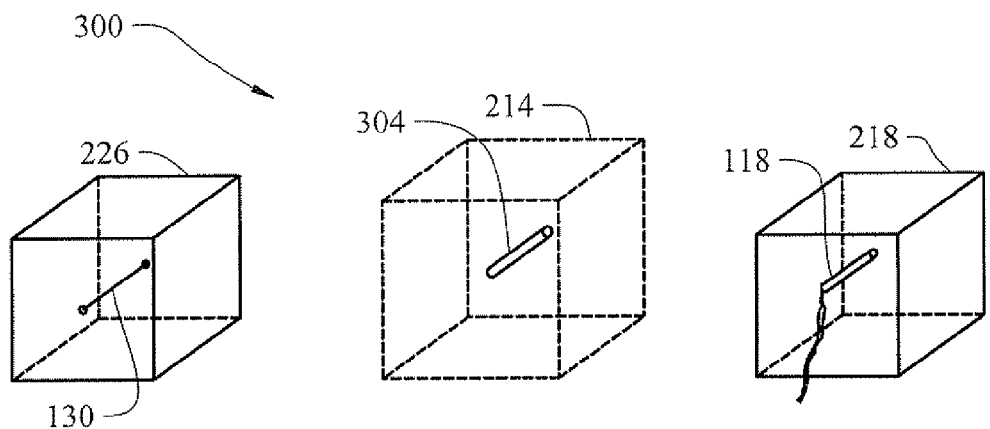
FIG. 3 is a perspective view of virtual and real spaces in accordance with one implementation of the present invention.

Not only the real stylus 130, but also the medical device 118 could be registered in the virtual display space 214. For example, virtual and real spaces in accordance with one such implementation are indicated generally in FIG. 3 by reference number 300. A representation 304 of the medical device 118 is provided within the 3D display system 126 as a "virtual device", suitably registered initially with the real device 118 by locating the real device 118 on fluoroscopic images, from device localization data, and/or other means. The stylus 130 also is registered with the virtual device 304. A user thus can manipulate the virtual device 304 in the 3D display space 214 using the stylus 130.

The system 100 uses a mathematical model to suitably interpret motions of the stylus 130 as manipulations of the virtual device 304 inside a constrained anatomy. The system 100 also uses a computational model to convert manipulations of the virtual device 304 into suitable control variables and/or changes in control variables that are used by the navigation system 116 to actuate the real medical device 118 in a corresponding manner. Thus the user can drag or move the real device 118 in near real-time to a suitable anatomical destination by manipulating the virtual device 304 in the 3D display space 214. In a preferred embodiment, the navigation system 116 actuates the real device 118 by means of a magnetic field and a device advancer to suitably deflect and position the medical device 118 within the patient. However, other or additional actuation methods and/or systems could be used, including but not limited to mechanical, electrostrictive and/or other means known to those skilled in the art.

Figure 4:
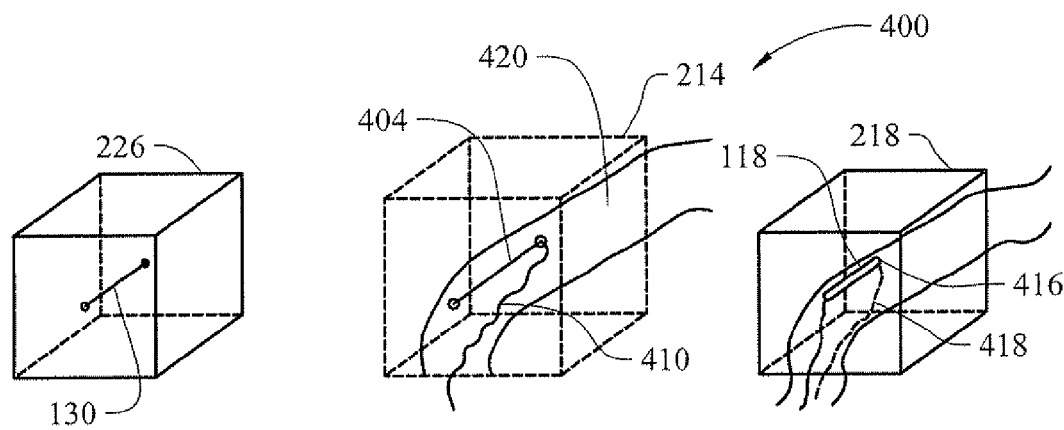
FIG. 4 is a perspective view of virtual and real spaces in accordance with one implementation of the present invention.

Virtual and real spaces in accordance with another implementation of the present invention are indicated generally in FIG. 4 by reference number 400. A user can use a virtual stylus 404 to define a path 410 in three dimensions for navigation purposes. The path 410 could be defined to include constraints. For example, constraints could be computationally modeled based on anatomical data and applied to the path 410. Additionally or alternatively, the user could use the stylus 130 to introduce constraints to the path 410 based, for example, on visual images from the imaging system 110. The real device 118 would be actuated suitably, in response to control variable changes computed based on the path 410 defined by the user and applied by the navigation system 116 as actuations to the device 118. Thus, for example, where the device 118 includes a magnetic tip 416 actuated by the navigation system 116, the device tip 416 could be actuated to follow a path 418 in the subject space 218, as defined by the user in near real-time in the virtual space 214. As more fully described in U.S. patent application Ser. No. 10/962,174, entitled Surgical Navigation with Overlay on Anatomical Images, incorporated herein by reference. Alternatively, the three-dimensional virtual path 410 can be defined, for example, at the beginning of a medical procedure, and the real device 118 can be suitably actuated during the procedure so that the tip of the device 118 follows the real path 418 defined by the virtual path 410.

The virtual path 410 can be overlaid on one or more fluoroscopic images 420 (including one or more live images) to provide a reference for comparison with movement of the real device 118. Additionally, one or more images of selected regions of the patient anatomy, such as vessel branching or bifurcations (vasculature or lung airways), heart chambers, etc. (selected, for example, from the 3D display space 214) could be overlaid on the image(s) 420.

Figure 5:
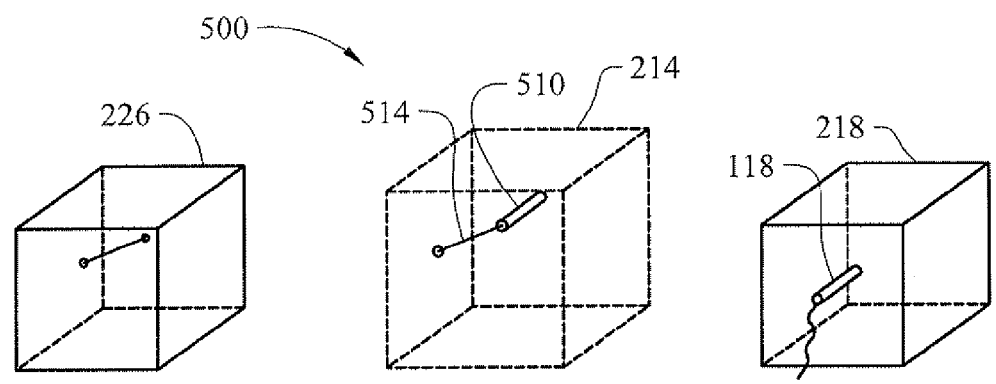
FIG. 5 is a perspective view of virtual and real spaces in accordance with one implementation of the present invention.

Virtual and real spaces in accordance with another implementation are indicated generally in FIG. 5 by reference number 500. A localized position of the real device 118 can be displayed within the 3D display space 214 as a real-time reference 510. A virtual stylus 514, to which the real stylus 130 is registered, could be used to manipulate the localized, virtually rendered device 510 to interactively control the real device 118 in a remote manner by means of the navigation system 116.

As previously mentioned with reference to FIG. 1, the user interface 124 can also provide a haptic interface. In such a configuration, the stylus 130 could be used to provide haptic feedback in coordination with the 3D display system 126. In another configuration, haptic feedback could be provided in coordination with a two-dimensional graphical interface such as a standard computer screen. An example of an input device that provides haptic feedback is a Phantom® device manufactured by SensAble Technologies, Inc.® of Woburn, Mass.

In a configuration that includes haptics, navigation of the medical device 118 by a user may be restricted in a manner that can be perceived intuitively by the user. Information can be conveyed to the user, for example, about anatomical boundaries or walls or about other medical devices that may have been inserted in the patient anatomy. Anatomical features of the patient are registered to coordinates of the navigation system 116. A space and/or coordinates of a haptic device, e.g., the stylus 130, also are registered to coordinates of the navigation system 116. After the anatomical features and haptic device are registered, the user may define boundaries visually, e.g., using fluoroscopic localization of a discrete set of points and/or lines, which information may be converted to surface data by one or more algorithms operating in the navigation system 116. Additionally or alternatively, three dimensional image data, e.g., CT and/or MR data taken preoperatively and/or intraoperatively, could be used to provide anatomical information in terms of surfaces and/or volumes. Similarly, intraoperative three-dimensional anatomical data obtained from the localization system 122 could also be used. Such data could be used to provide haptic feedback by which the user may sense, for example, when a requested destination location is out of range of a particular region of anatomy, or when a localized medical device slaved to a stylus reaches an anatomical boundary as determined from three dimensional anatomical data, or when a virtually rendered stylus touches an anatomical wall within a three-dimensional display, or when the real stylus 130 touches a virtual anatomical surface within the region of operation of the stylus 130. Targets for device navigation can be intuitively defined with such an interface. For example, haptic input could be used to assist the user in defining a navigation target relative to a path that includes constraints as previously described with reference to FIG. 4.

In still another embodiment, data describing an anatomical surface can be used to make the surface seem "magnetically attractive". That is, when the stylus 130 is in a location that corresponds to the device 118 being within a predefined range of the anatomical surface, e.g., a body wall, a suitably defined force-field can be applied to the hand-held stylus 130 to pull the user's hand and stylus 130 to a position corresponding to the wall. Thus the user can, in an intuitive manner, cause the device 118 be constrained to an anatomical surface for various procedural purposes. The foregoing method can also be used for selecting desired navigational locations and/or selecting locations to be marked or annotated on the anatomical surface.

In a further embodiment, data describing an anatomical wall could be used to make the wall seem, for example, "hard", "semi-hard", or "squishy" relative to the stylus 130 in order to provide a haptic cue to the user that the stylus 130 has reached a location corresponding to the wall. This cueing could be accomplished, for example, in conjunction with a virtual stylus rendered within the 3D display system 126 or in a display on a two-dimensional computer screen, or without displaying a virtual stylus. Additionally or alternatively, haptic feedback could be used to enforce one or more zones of restricted navigation or "virtual constraints" defined to prevent the medical device 118 from accessing anatomical regions outside such zone(s).

Given the spatially complex navigation that is typically required in surgical procedures, an inherently three-dimensional interface to a remote navigation system provides numerous advantages. The foregoing display system allows an operating physician to perceive the various depths of convoluted sites in which a medical device is typically navigated. He or she can actuate the medical device by using three-dimensional manipulations more instinctually related to physical movement of the device than manipulations used, for example, to operate a joystick or mouse. Learning to use configurations of the present system is easier and faster than learning to operate a two-dimensional user interface. Configurations in which a haptic three-dimensional input device is used as described above can significantly enhance the ease of use of a remote navigation system. A physician can interact more effectively with a remote navigation system to control a medical device when configurations of the foregoing control system are used.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for controlling a medical device in a patient comprising:
    a display system that displays an image of at least part of a volume of the patient in a virtual three-dimensional space, wherein the medical device is registered to coordinates of the virtual three-dimensional space such that a virtual reference device is provided in the virtual three-dimensional space;
    a stylus registered with the virtual three-dimensional space such that a virtual element is provided in the virtual three-dimensional space, where the stylus is controllable to actuate the virtual element in the virtual three-dimensional space, and wherein the stylus is registered to the virtual reference so that the virtual reference can be manipulated in the virtual three-dimensional space by the stylus; and
    a navigation system that controls the medical device in the patient volume based on a position of the actuated virtual element.

2. The system of claim 1 further comprising a device localization system that obtains a position of the medical device and provides the device position to the navigation system; wherein the navigation system uses the device position to control the medical device.

3. The system of claim 1 wherein the stylus is controllable to actuate the virtual element to define a path in the virtual space, and wherein the navigation system navigates the medical device in the subject in accordance with the path.

4. The system of claim 1 wherein the stylus is controllable to actuate the virtual element to define a target location in the virtual space, and the navigation system navigates the medical device in the patient to the defined target location.

5. The system of claim 1 wherein:
    the display system displays the medical device as a reference in the virtual space;
    the stylus is controllable to actuate the virtual element to actuate the reference; and
    the navigation system controls the medical device based on the actuated reference.

6. The system of claim 1 wherein the stylus provides haptic feedback to the user.

7. A system for controlling a medical device in an operating volume in a subject, the system comprising:
    a device localization system that determines a position of the medical device in the operating volume in the subject, wherein the medical device is registered to coordinates of a virtual three-dimensional space such that a virtual reference device is provided in the virtual three-dimensional space;
    a navigation system that controls the position of the device in the operating volume in the patient based at least in part upon the position determined by the device localization system;
    a stylus controllable in a real space, wherein the stylus is registered with the virtual three-dimensional space such that a virtual three-dimensional element is provided in the virtual three-dimensional space; and
    a display system that displays the medical device as a virtual three-dimensional reference and the stylus as a virtual three-dimensional element relative to an image of at least part of the patient volume, and communicates a position of the virtual element to the navigation system, wherein the stylus is also registered to the virtual three-dimensional reference so that the virtual reference may be manipulated in the virtual three-dimensional space by the stylus;
    wherein the navigation system uses the virtual element position as an input to control the medical device.

8. A system for controlling a medical device in an operating volume in a subject, the system comprising:
    a device localization system that determines the position of the medical device in the operating volume in the subject, wherein the medical device is registered to coordinates of a virtual three-dimensional space such that a virtual reference device is provided in the virtual three-dimensional space;

a navigation system that controls the medical device in the operating volume in the subject based on the determined position;

a stylus controllable in a real space outside the operating volume, wherein the stylus is registered with the virtual three-dimensional space such that a virtual three-dimensional element is provided in the virtual three-dimensional space, and the stylus is also registered to the virtual three-dimensional reference so that the virtual reference may be manipulated in the virtual three-dimensional space by the stylus, the navigation system changing the position of the medical device in the operating volume based upon changes in the position of the stylus in the real space.

9. The system of claim 8, where the stylus provides haptic feedback to the user.

10. A system for controlling a medical device in an operating volume in a subject, the system comprising:

a device localization system that determines the position of the device in the operating volume in the subject, wherein the medical device is registered to coordinates of a virtual three-dimensional space such that a virtual device is provided in the virtual three-dimensional space;

a navigation system that controls the medical device in the operating volume in the subject based on the determined position;

a real stylus registered with the virtual three-dimensional space such that a virtual stylus is provided in the virtual three-dimensional space, wherein the stylus is also registered to the virtual device so that the virtual device can be manipulated in the virtual three-dimensional space by the stylus, said stylus being controllable in a real space to cause the virtual stylus to move the virtual device in a virtual space; and wherein the navigation system controls the position of the distal end of the medical device in response to the position of the virtual device.

11. The system of claim 10, where the stylus provides haptic feedback to the user.

12. The system of claim 11, wherein the navigation system comprises a source for applying a magnetic field to the operating volume, and the medical device comprises at least one magnetically responsive element that can be oriented by the magnetic field applied by the source.

13. A method of controlling a medical device in a patient comprising:

registering a stylus with the coordinates of a virtual three-dimensional space such that a virtual element may be provided in the virtual three-dimensional space, where the stylus is controllable to actuate the virtual element in the virtual three-dimensional space;

registering the stylus with a representation of the medical device so that the representation can be manipulated in the virtual three-dimensional space by the stylus;

moving the stylus in a real space to actuate the virtual element relative to the virtual three-dimensional space corresponding to a volume of the patient; and observing, in the virtual three-dimensional space, the representation of the medical device actuated in the patient volume in accordance with the actuated virtual element.

14. A system for controlling a medical device within a patient, comprising:

a display that displays an image of at least part of a volume of a patient in a virtual three-dimensional space in which the medical device and a real stylus are registered such that a virtual device corresponding to the medical device and a virtual element corresponding to the real stylus is displayed in the virtual three-dimensional space, the real stylus also being registered to the virtual device so that the virtual device can be manipulated in the display of the virtual three-dimensional space by the real stylus wherein the display converts movement of the real stylus to virtual movement of the virtual element;

a navigation system that uses the virtual movement to control the medical device; and an imaging system that provides at least one image of a patient volume to at least one of the navigation system and the display system;

wherein the virtual element is displayed in three virtual dimensions relative to the at least one image.

15. A system for controlling a medical device within a patient, comprising:

a navigation system that uses actuation control variables to control the medical device;

a display that displays an image of at least part of a volume of a patient in a virtual three-dimensional space in which the medical device and a real stylus are registered such that a virtual device corresponding to the medical device and a virtual stylus corresponding to the real stylus is displayed in the virtual three-dimensional space, the real stylus also being registered to the virtual device so that the virtual device can be manipulated in the display of the virtual three-dimensional space by the real stylus;

an interface system that converts movement of the real stylus to virtual movement of the virtual stylus, and converts the virtual movement to actuation control variables of the navigation system; and an imaging system that provides at least one image of a patient volume to at least one of the navigation system and the interface system.

16. A method of displaying a medical device within a patient, comprising:

registering a stylus with the coordinates of a virtual three-dimensional space such that a virtual element may be provided in the virtual three-dimensional space, where the stylus is controllable to actuate the virtual element in the virtual three-dimensional space;

registering the stylus with a representation of the medical device so that the representation can be manipulated in the virtual three-dimensional space by the stylus;

receiving data describing movement of the stylus;

displaying the virtual element in three virtual dimensions in accordance with the stylus movement data;

providing data describing the virtual element to a navigation system that actuates the medical device in the patient based on the virtual element data and provides data describing actuation of the medical device; and displaying the virtual element in accordance with the medical device actuation data.

17. The method of claim 14, wherein displaying the virtual element further comprises displaying at least one image describing at least part of a volume of the patient in which the medical device is actuated.

18. A system for controlling a medical device within an operating region in a subject, comprising:

a navigation system that controls the orientation of the distal end of a medical device in response to actuation control variables;

a display that displays an image of at least part of a volume of a subject in a virtual three-dimensional space in which the medical device and a real stylus are registered such that a virtual device corresponding to the medical device and a virtual stylus corresponding to the real stylus is displayed in the virtual three-dimensional space, the real stylus also being registered to the virtual device so that the virtual device can be manipulated in the display of the virtual three-dimensional space by the real stylus;

an interface system that converts movement of the real stylus operated by a user to actuation control variables for the navigation system; and wherein the display incorporates a representation of the virtual stylus together with three dimensional anatomical data that is registered to the navigation system, and where movements of the virtual stylus are matched with movements of the real stylus.

19. The system of claim 18, where the stylus provides haptic feedback to the user.

20. A method for controlling a medical device within a patient, comprising:

orienting the distal end of a medical device using a navigation system, in response to actuation control variables to control the medical device;

registering a real stylus with the coordinates of a virtual three-dimensional space such that a virtual element may be provided in the virtual three-dimensional space, where the real stylus is controllable to actuate the virtual element in the virtual three-dimensional space;

registering the real stylus with the representation of the medical device so that the representation can be manipulated in the virtual three-dimensional space by the real stylus;

converting movement of the real stylus operated by a user to actuation control variables for the navigation system; and displaying on a display a representation of a registered, localized device incorporated with three dimensional anatomical data that is registered to the navigation system, where movements of the real stylus are converted through said actuation control variables to movements of the medical device.

21. The method of claim 20, where the stylus provides haptic feedback to the user.

22. The method of claim 20, where the stylus controls the orientation of the medical device.

23. The method of claim 22, where the stylus provides haptic feedback to the user.

24. The method of claim 20, where the three dimensional anatomical data is acquired intraoperatively.

25. The method of claim 24, where the three dimensional anatomical data represents an anatomical surface.

26. The method of claim 18, where the three dimensional anatomical data represents an anatomical surface.

27. The method of claim 26, where the three dimensional anatomical data is acquired intraoperatively.

28. A system for controlling a medical device within a patient, comprising:

a display that displays an image of a virtual three-dimensional space apart from the operating volume in the patent;

a medical device in the operating volume in the patient, wherein positional data associated with the medical device is registered to coordinates of the virtual three-dimensional space, such that a virtual reference device is provided within the virtual three-dimensional space;

a stylus controllable in a real space outside the operating volume of the patient, where the stylus is registered with the virtual three-dimensional space, such that a virtual stylus is provided within the virtual three-dimensional space that is actuated by movement of the stylus in real space, wherein the stylus is also registered with the virtual reference device so that the virtual reference device can be manipulated in the virtual three-dimensional space using the stylus;

wherein the display incorporates a representation of the virtual stylus and the virtual reference device together with three dimensional anatomical data that is registered to the navigation system, where movements of the virtual stylus are matched with movements of the real stylus;

an interface system that converts movement of the virtual stylus actuated by a user and/or movements of the virtual reference device to actuation control variables for a navigation system; and a navigation system that controls the orientation of the distal end of a medical device in response to actuation control variables.

29. The system of claim 28 wherein the stylus is controllable to actuate the virtual stylus to define a path for the virtual reference device in the display of the virtual three-dimensional space, and wherein the navigation system navigates the medical device in the subject in accordance with the path.

30. The system of claim 28 wherein the stylus is controllable to actuate the virtual stylus to define a target location for the virtual reference device in the display of the virtual three-dimensional space, and the navigation system navigates the medical device in the patient to the defined target location.

* * * * *